(12) United States Patent
Lawrence (10) Patent No.: US 6,508,790 B1
(45) Date of Patent: Jan. 21, 2003

(54) VASCULAR ACCESS SHEATH

(76) Inventor: William K. Lawrence, 4711 Sunningdale Dr., Belden, MS (US) 38826

( * ) Notice: Subject to any disclaimer, the term of this patent is extended or adjusted under 35 U.S.C. 154(b) by 78 days.

(21) Appl. No.: 09/680,967

(22) Filed: Oct. 6, 2000

Related U.S. Application Data (60) Provisional application No. 60/164,933, filed on Nov. 15, 1999.

(51) Int. Cl.[7] .............................................. A61M 5/178
(52) U.S. Cl. ................................................. 604/167.05
(58) Field of Search ............................... 604/5.02, 5.04, 604/6.09, 6.11, 19, 29, 30, 93.01, 158, 164.01, 32, 167.01, 167.03, 167.05, 9

(56) References Cited

U.S. PATENT DOCUMENTS

| | | | |
|---|---|---|---|
| 3,595,230 A | | 7/1971 | Suyeoka et al. |
| 4,392,853 A | | 7/1983 | Muto |
| 4,547,194 A | | 10/1985 | Moorehead |
| 4,551,137 A | | 11/1985 | Osborne |
| 4,619,643 A | | 10/1986 | Bai |
| 4,634,433 A | | 1/1987 | Osborne |
| 4,643,711 A | | 2/1987 | Bates |
| 4,758,336 A | | 7/1988 | Bock et al. |
| 4,892,518 A | | 1/1990 | Cupp et al. |
| 4,913,704 A | | 4/1990 | Kurimoto |
| 5,092,846 A | * | 3/1992 | Nishijima et al. |
| 5,106,368 A | | 4/1992 | Uldall et al. |
| 5,250,038 A | * | 10/1993 | Melker et al. |
| 5,256,150 A | * | 10/1993 | Quiachon et al. |
| 5,409,461 A | * | 4/1995 | Steinman |
| 5,417,665 A | * | 5/1995 | De La Mata et al. |
| 5,423,762 A | * | 6/1995 | Hillstead |
| 5,474,534 A | * | 12/1995 | Schlitt |
| D367,324 S | | 2/1996 | McCarthy et al. |
| 5,599,305 A | * | 2/1997 | Hermann et al. |
| D381,418 S | | 7/1997 | Erskine et al. |
| D384,411 S | | 9/1997 | Musgrave et al. |
| 5,672,158 A | * | 9/1997 | Okada et al. |
| 5,676,656 A | * | 10/1997 | Brimhall |
| 5,681,288 A | | 10/1997 | Schlitt |
| 5,693,008 A | | 12/1997 | Brugger et al. |
| 5,693,025 A | | 12/1997 | Stevens |
| 5,697,914 A | | 12/1997 | Brimhall |
| 5,722,959 A | | 3/1998 | Bierman |
| 5,727,555 A | | 3/1998 | Chait |
| 5,755,702 A | | 5/1998 | Hillstead |
| 5,779,681 A | | 7/1998 | Bonn |
| 5,807,311 A | | 9/1998 | Palestrant |
| 5,843,031 A | | 12/1998 | Hermann et al. |
| 6,190,371 B1 | * | 2/2001 | Maginot et al. ............ 604/171 |

FOREIGN PATENT DOCUMENTS

WO     WO 93/13822     7/1993

* cited by examiner

*Primary Examiner*—Michael J. Hayes
*Assistant Examiner*—Michelle Lewis
(74) *Attorney, Agent, or Firm*—Richard C. Litman (57) ABSTRACT

A permanent or semipermanent hemodialysis access sheath that is placed in a central vein, secured and left in place for easy access by a removable hemodialysis catheter. The hemodialysis catheter has an adapter which secures the catheter to the sheath temporarily permitting the easy removal and replacement of the catheter as needed. The sheath has a side tube with a rotating flush valve. The sheath has a threaded opening which may be engaged by a threaded hub on the hemodialysis catheter for temporaraily securing the catheter to the sheath.

7 Claims, 6 Drawing Sheets

VASCULAR ACCESS SHEATH

CROSS-REFERENCE TO RELATED APPLICATION

This application claims the benefit of U.S. Provisional Patent Application Ser. No. 60/164,933, filed Nov. 15, 1999.

BACKGROUND OF THE INVENTION

1. Field of the Invention

The present invention relates to a permanent or semipermanent hemodialysis access sheath and an adapter for a hemodialysis catheter.

2. Description of Related Art

Hemodialysis is a procedure for removing metabolic waste products or toxic substances from the bloodstream by dialysis. Dialysis, in terms of hemofiltration, is the process of separating elements in a solution by convective transport of solute through ultrafiltration across a semipermeable membrane down a concentration gradient. Convective solute transport depends on the movement of dissolved substances concomitant with fluid flow through a filtering membrane.

Hemodialysis requires extracorporeal circulation of the blood. Blood is removed from the patient via a suitable access and pumped to the membrane unit. Dialyzed blood is returned to the patient through tubing that incorporates an air embolus protector.

Typically, long-term access to the circulation is provided by subcutaneous arteriovenous fistulas. Temporary access to the circulation may be achieved by inserting single- or double-lumen catheters into the subclavian or femoral veins. Most subclavian catheters are useful for hemodialysis over 2 to 6 weeks when strict skin care protocols are followed and the use of the catheter is limited to hemodialysis and hemofiltration procedures. Some designs are made of silicone rubber and have a subcutaneous fabric cuff. The latter has a longer life span and may be used for chronic hemodialysis in those patients for whom it is impossible to create a conventional access.

Current chronic type hemodialysis access catheters are placed in a large central vein usually in patients who have exhausted all other means of hemodialysis access or who are awaiting maturation of an A-V fistula. These catheters have a limited life span from many causes, chiefly fibrin sheath development and thrombosis. They are also prone to malfunction because of suboptimal positioning. Once these catheters fail, they must be surgically removed and surgically replaced in another vein. Over time, the venous access sites become exhausted.

Both catheters and sheaths have been the subjects of previous patents. U.S. Design Pat. No. 384,411 shows an ornamental design for a double lumen catheter with a guidewire retainer. U.S. Pat. No. 3,595,230 discloses a catheter placement unit which includes a catheter shield, catheter and needle for use in venipuncture. U.S. Pat. No. 4,913,704 discloses a disposable indwelling catheter placement unit which includes a plastic catheter and a plastic sheath having a slit. U.S. Pat. No. 5,676,656 shows a control forward introducer needle and catheter assembly. U.S. Pat. No. 5,697,914 shows a control forward and flashback forward one hand introducer needle and catheter assembly for use when introducing fluid intravenously.

U.S. Patent Nos. 4,551,137 and 4,634,433 describe a flexible sheath which maintains the sterility of the exposed portion of an indwelling catheter. U.S. Pat. No. 4,619,643 shows a double lumen catheter for use in hemodialysis. U.S. Pat. No. 5,250,038 shows a multiple lumen vascular access introducer sheath having a main lumen for introducing another device, and a secondary lumen having a significantly smaller cross-sectional area for infusion of small doses of medication. U.S. Pat. No. 5,256,150 discloses a large-diameter expandable sheath for use in introducing a catheter into a vessel. U.S. Pat. Nos. 5,599,305 and 5,843,031 disclose a large-diameter introducer sheath which has a hemostasis valve and removable steering mechanism. U.S. Pat. No. 5,779,681 discloses a stiff tubular catheter segment which is designed to remain outside the body. None of the above patents for catheters and sheathes disclose hubs or flanges for holding a sheath to a catheter for long term use and replacement, nor do they provide for permanent placement of a sheath or a catheter in a venous cavity.

U.S. Pat. No. 4,392,853 issued to Muto on Jul. 12, 1983 discloses a sterile assembly for protecting and fastening an indwelling device such as an elongated catheter or pacer lead in an incision. The invention of Muto utilizes a clamp to hold a length of an indwelling device, such as a catheter, in place. The clamp is secured external to the body near the incision. No provision is made for removing the indwelling device and replacing the indwelling device without removing the clamp and reinserting the entire apparatus again.

U.S. Pat. No. 4,547,194 issued to Moorehead on Oct. 15, 1985 discloses an apparatus and method which includes a catheter and a hub, and a method for inserting, extending and repairing the exposed (external) end of the catheter. The hub is connected to the exposed end of an indwelling pliant catheter tube in order to facilitate extending the catheter with additional lengths. The invention of Moorehead does not provide for the removal and replacement of an indwelling catheter nor does it provide an apparatus to secure the catheter in place.

U.S. Pat. Nos. 4,643,711 and 4,772,268, issued to Bates on Feb. 17, 1987 and Sep. 20, 1988 respectively, disclose a dual lumen hemodialysis catheter which includes a tube having circular external cross section that is rotatably received within a fitting. The fitting is designed to be attached to the patient by sutures or the like. The catheter is kept from moving longitudinally relative to the fitting but is allowed to freely rotate. The invention of Bates does not provide an easily replaceable catheter since the fitting must be removed in order to replace the catheter.

U.S. Pat. No. 5,106,368 issued to Uldall et al. on Apr. 21, 1992 discloses a dual lumen catheter, for providing extracorporeal treatment such as hemodialysis, which is percutaneously inserted for either short-term or long-term vascular access. A ring-like grommet moveable along the proximal segment of the catheter anchors the catheter to the surrounding tissue via a flange extending from the grommet. Sutures are utilized to hold the grommet in to place. The grommet can be released by pulling on it or by dissecting it out; there is no bleeding associated with the release of the grommet. The catheter is left in place. There is no provision in the invention of Uldall et al. for the insertion and maintenance of a sheath in place instead of fixing the catheter in place. To replace the catheter, the supraclavicular incision must be reopened and the subcutaneous sutures anchoring the grommet in place must be removed.

U.S. Pat. Nos. 5,474,534 and 5,681,288, issued to Schlitt on Dec. 12, 1995 and Oct. 28, 1997 respectively, disclose an indwelling catheter having a tab which can be rotated against the skin and taped into place with a strip of adhesive tape. The tab is utilized in inserting the catheter into a subcutaneous vein, artery or other blood vessel, and then the tab serves to prevent the catheter from rotating or moving longitudinally once secured into place. Specifically, the catheter of Schlitt is designed to introduce liquids directly into the blood stream. The catheter of Schlitt is not designed to be left in place long term nor is a sheath utilized for removing and replacing the catheter.

U.S. Pat. No. 5,672,158 issued to Okada et al. on Sep. 30, 1997 shows a catheter introducer which allows a dilator section and a sheath section to be readily engaged with and disengaged from each other. The catheter introducer has a sheath, a sheath hub, a dilator, and a dilator hub. The dilator hub includes a flange to cover the end of the sheath hub. The catheter introducer of Okada et al. is specifically intended to introduce a catheter into a blood vessel such as for angiography. The invention is particularly designed to prevent the relative rotation and axial displacement of the dilator with respect to the sheath during introduction of a catheter. The sheath is not designed to remain in place long term. The significance of the invention of Okada et al. is on the means of engaging the dilator and the sheath in order to prevent undesirable movement of the sheathe relative to the dilator. No provision is made for removably attaching the sheath to the catheter in order to secure the catheter in place for long term usage.

U.S. Pat. No. 5,693,025 issued to Stevens on Dec. 2, 1997 discloses a medical adapter having a hemostasis valve and a rotatable connector. The rotatable connector disclosed in Stevens is at the end of the adapter, and is for connection end-to-end to a catheter, needle, or such. The rotatable connector is not midway down a tube or catheter and could not be used to hold a catheter in place relative to a sheath but instead is used to attach a needle, catheter, introducer or such to an adapter in order to add more input lines so that the catheter or needle will not need to be removed and reinserted in the patient for different medical devices.

U.S. Pat. No. 5,722,959 issued to Bierman on Mar. 3, 1998 shows a catheter securement device which retains an indwelling catheter at a desired incident angle while allowing incremental adjustments of the incident angle without disconnecting the catheter from the retainer. The retainer includes an arcuate slot which curves toward an insertion site of the indwelling catheter. The slot receives a portion of a hub of the catheter. The retainer has protrusions which project into the slot and capture a hub of the catheter at discrete positions within the slot thus assuring the catheter is held securely in a proper angle. The retainer connects to an anchoring base which secures the retainer to the patient's skin proximate to the catheterization site. The device of Bierman is designed to aid in placing an indwelling catheter or similar device and to hold an indwelling catheter or similar device in place once correctly positioned. The invention of Bierman does not alleviate the need to periodically remove the catheter and does not permit the reinsertion of the catheter in the same venous cavity, nor does it allow for the securing of a sheath in place for that purpose.

U.S. Pat. No. 5,807,311 issued to Palestrant on Sep. 15, 1998 discloses a dialysis catheter having rigid and collapsible lumens, and a method for using the dialysis catheter. The dialysis catheter has a suture wing which is used to secure the catheter in place in the venous system. The catheter disclosed in Palestrant does reduce the likelihood of blood clot formation but does not facilitate the easy removal of the catheter without damaging the catheterization site. The invention of Palestrant does not provide for permanent placement of a sheath which could be utilized to hold a catheter in place thus allowing the removal and replacement of the catheter as needed.

None of the above inventions and patents, taken either singly or in combination, is seen to describe the instant invention as claimed.

SUMMARY OF THE INVENTION

The present invention is a permanent or semi-permanent vascular access sheath for hemodialysis access for patients in renal failure. Included in the present invention is an adapter for a hemodialysis catheter which is designed to be used with the vascular access sheath disclosed herein. My design preserves venous access by placing a chronic sheath, instead of a chronic catheter, in a central vein. The hemodialysis catheter is placed via the sheath.

The hemodialysis catheter has the additional properties of a rotating flange and hub which serve to secure the catheter in place. The catheter attaches to the vascular access sheath via the hub and is secured into place by the rotating flange thus reducing the possibility that the catheter will move longitudinally independent of the sheath once inserted and attached. When the catheter fails, it can be easily removed and replaced without surgery, and without losing venous access. The length of the catheter can vary for optimal placement. Also, fibrin sheaths can be disrupted with an angioplasty balloon inflated beyond the sheath tip.

Accordingly, it is a principal object of the invention to provide a hemodialysis access sheath which can be permanently or semi-permanently placed in the venous system of a patient requiring hemodialysis. The access sheath can be secured and maintained safely in place via a stitch loop and a band cuff made of Dacron™, a synthetic polyester fiber.

It is another object of the invention to provide a hemodialysis access sheath which will maintain the integrity of the venous access and permit the replacement of a hemodialysis catheter without requiring surgery. The present invention helps preserve venous access sites by permitting the removal and replacement of a hemodialysis catheter without damaging the access site. The initial placement of the access sheath is the only surgical procedure needed for venous access.

It is a further object of the invention to provide an adapter for a hemodialysis catheter which will secure the catheter in position relative to the hemodialysis access sheath disclosed herein. The catheter has a hub which engages a threaded lip on the sheath's orifice thus securing the catheter in place relative to the sheath. Also, a flange having an interlocking tab is provided on the catheter which can be attached to an interlocking tab provided on the sheath.

Still another object of the invention is to reduce medical cost, morbidity and mortality related to the medical procedures involved in hemodialysis and concomitant complications found in the prior art. Because the access sheath of the present invention permits the removal and replacement of hemodialysis catheters without surgery, there is a concomitant reduction in complications and costs due to repeated surgical procedures. Also, the fact that fibrin sheaths can be disrupted with an angioplasty balloon inflated beyond the sheath tip helps preserve the venous access site and reduces other complications which may result from the untreated build up of fibrin sheaths.

It is an object of the invention to provide improved elements and arrangements thereof in an apparatus for the purposes described which is inexpensive, dependable and fully effective in accomplishing its intended purposes.

These and other objects of the present invention will become readily apparent upon further review of the following specification and drawings.

BRIEF DESCRIPTION OF THE DRAWINGS

Similar reference characters denote corresponding features consistently throughout the attached drawings.

DETAILED DESCRIPTION OF THE PREFERRED EMBODIMENT

Figure 1:
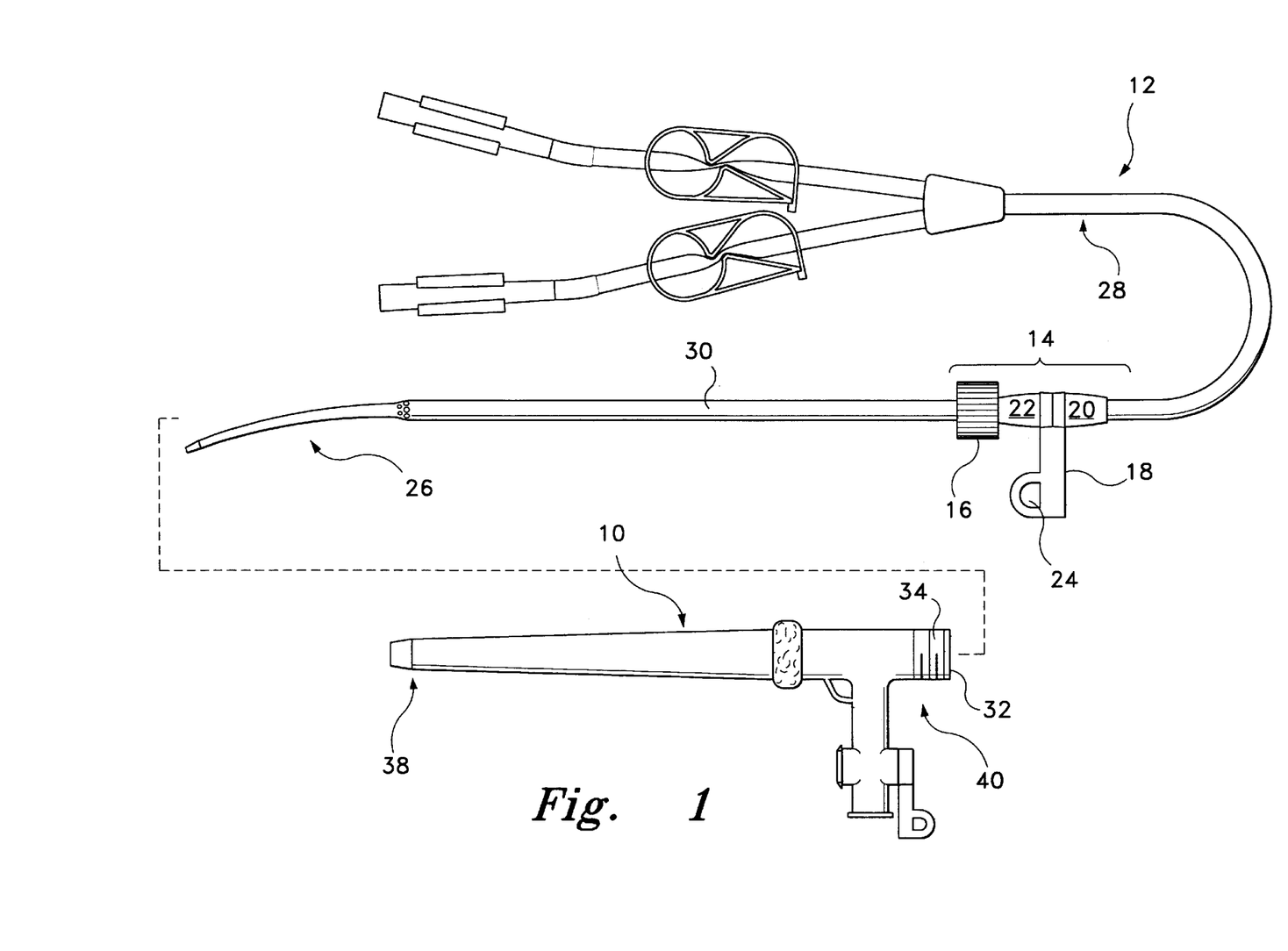
FIG. 1 is a perspective view of a hemodialysis access sheath and a hemodialysis catheter with adapter according to the present invention.

The present invention is a permanent or semipermanent hemodialysis access sheath and an adapter for a hemodialysis catheter. FIG. 1 shows the hemodialysis access sheath 10 and a modified hemodialysis catheter 12 as envisioned by the current invention. The broken line in FIG. 1 indicates where the modified hemodialysis catheter 12 inserts into the access sheath 10.

Figure 2:
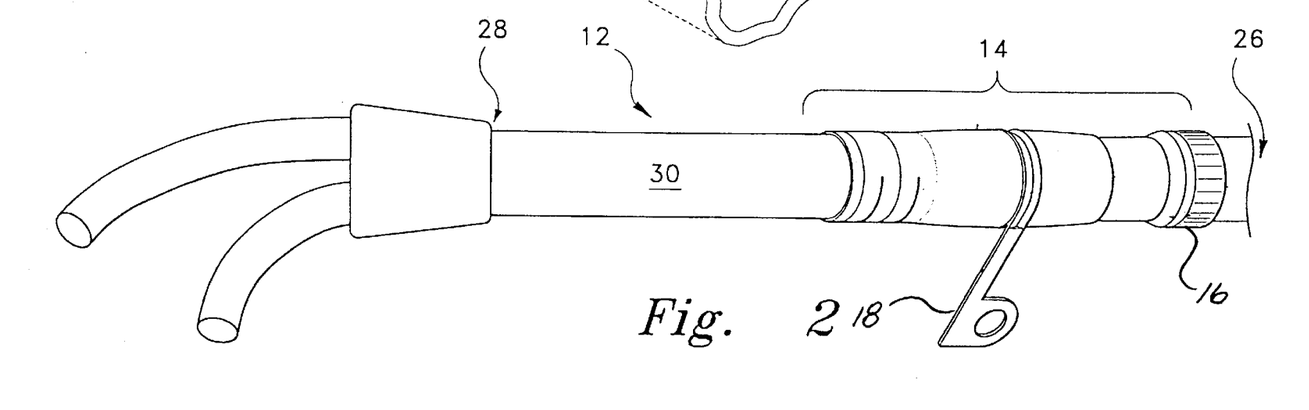
FIG. 2 is a perspective view of the catheter adapter.
Figure 3:
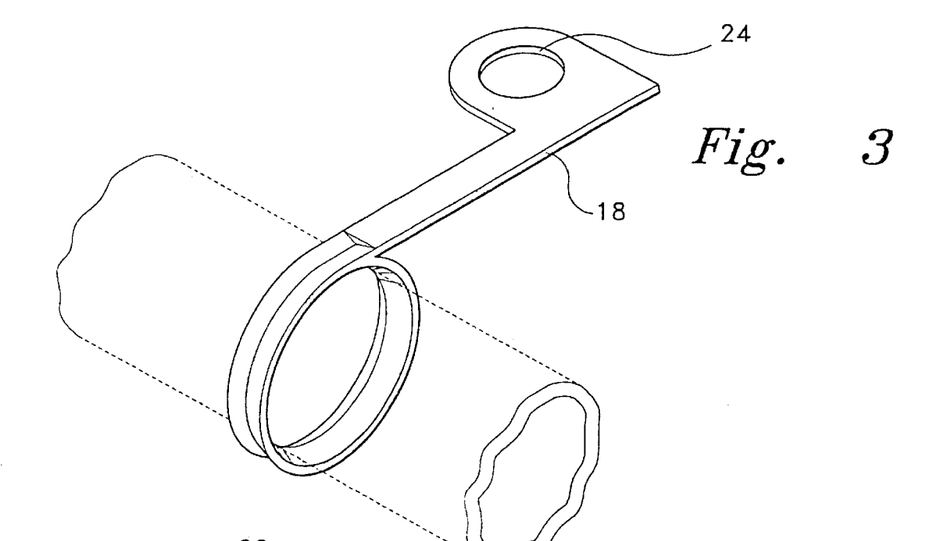
FIG. 3 is a perspective view of the rotating flange of the catheter adapter.
Figure 4:
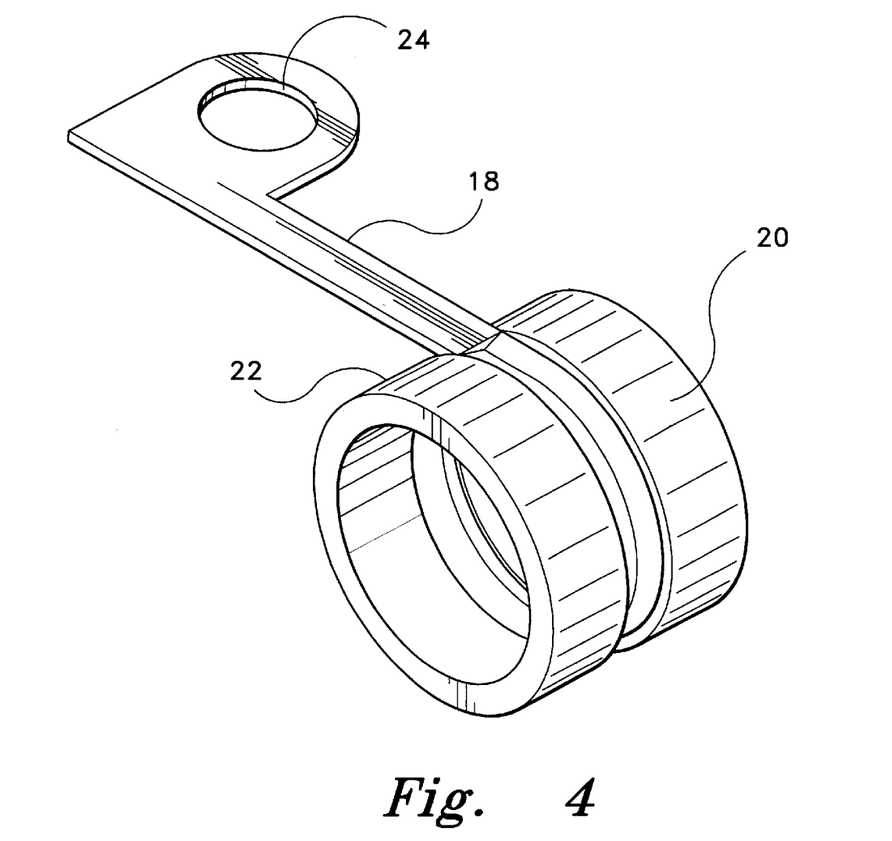
FIG. 4 is a perspective view of the rotating flange being flanked by the restriction bands.
Figure 5:
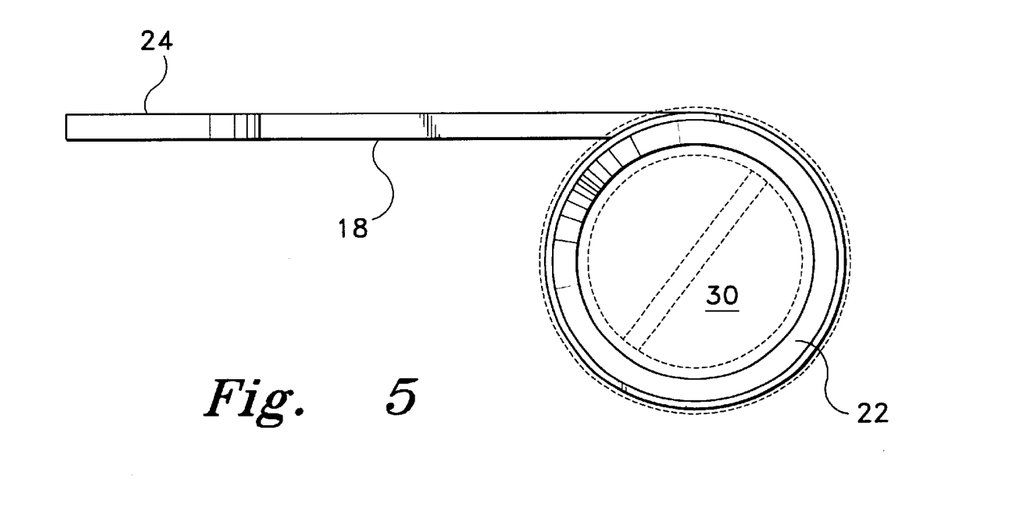
FIG. 5 is a side view of the rotating flange and restriction bands showing the lumen of the catheter.

The adapter 14, as shown in FIG. 2, can be affixed to any standard hemodialysis catheter. The hemodialysis catheter 12 has a catheter tube 30, a distal end 26, and a proximal end 28 as shown in FIGS. 1 and 2. The adapter 14 consists of a hub 16, a flange 18, a first restriction band 20, and a second restriction band 22. Ideally, the flange has a first interlocking tab 24. The hub 16 rotatably circumnavigates the tube of the catheter and has a threaded receptor opened towards the distal end 26 for receiving the threaded lip 34 of the sheath orifice 32 as discussed hereinafter. The flange 18 rotatably circumnavigates the catheter tube 30, as shown in FIGS. 3, 4, and 5. The flange 18 is located proximal to the hub 16 as shown in FIG. 2. The flange 18 is flanked by the first and second restriction bands 20 and 22 thus preventing axial movement of the flange 18 along the catheter tube. The first and second restriction bands 20 and 22 are tightly connected to the catheter tube.

Figure 9:
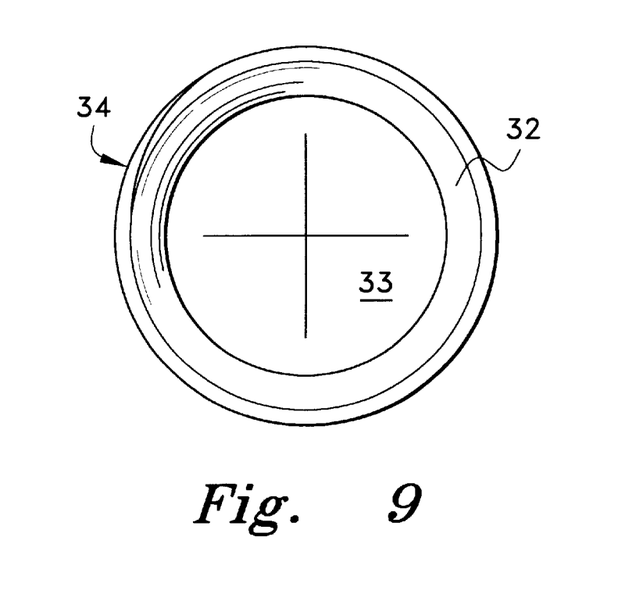
FIG. 9 is a top view of the sheath orifice showing the threaded lip and thin slit membrane.
Figures 10, 11:
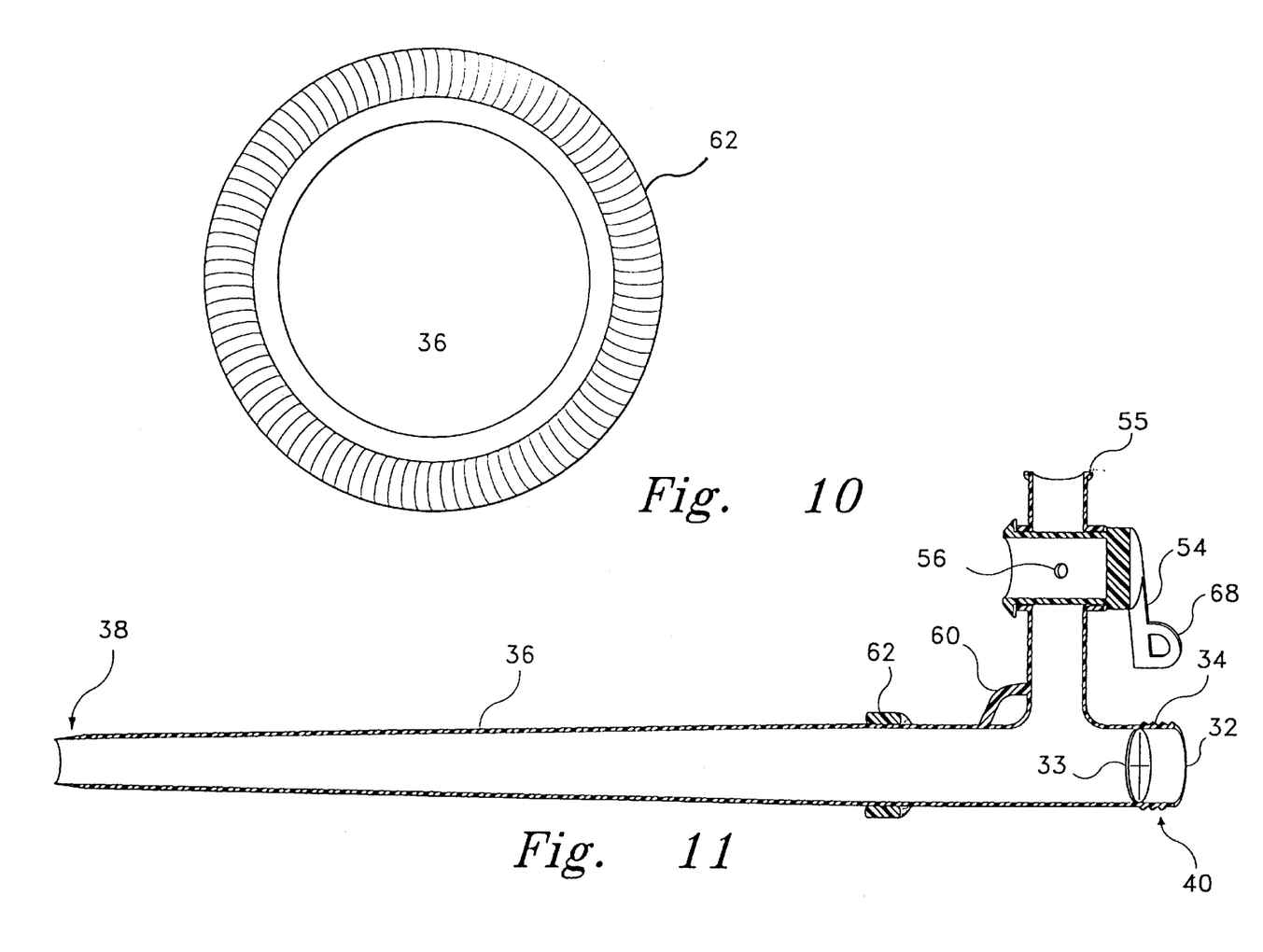
FIG. 10 is a cross sectional view of the hemodialysis access sheath, along the line 10—10 of FIG. 7, showing the Dacron™ polyester fiber cuff and the lumen of the sheath.
FIG. 11 is a cross sectional view along the axis of the hemodialysis access sheath according to the present invention.

The hemodialysis access sheath 10 has an elongated tube 36. The elongated tube 36 has a distal end 38 and a proximal end 40, the distal end 38 having a tapered opening as shown in FIGS. 1 and 11. On the proximal end 40 of the elongated tube 36 of the hemodialysis access sheath 10 there is a sheath orifice 32. The sheath orifice 32 has a threaded lip 34 which is received into the hub 16 of the adapter 14. Also, just inside the sheath orifice 32 is a thin slit membrane 33 as shown in FIGS. 9 and 11.

Figure 6:
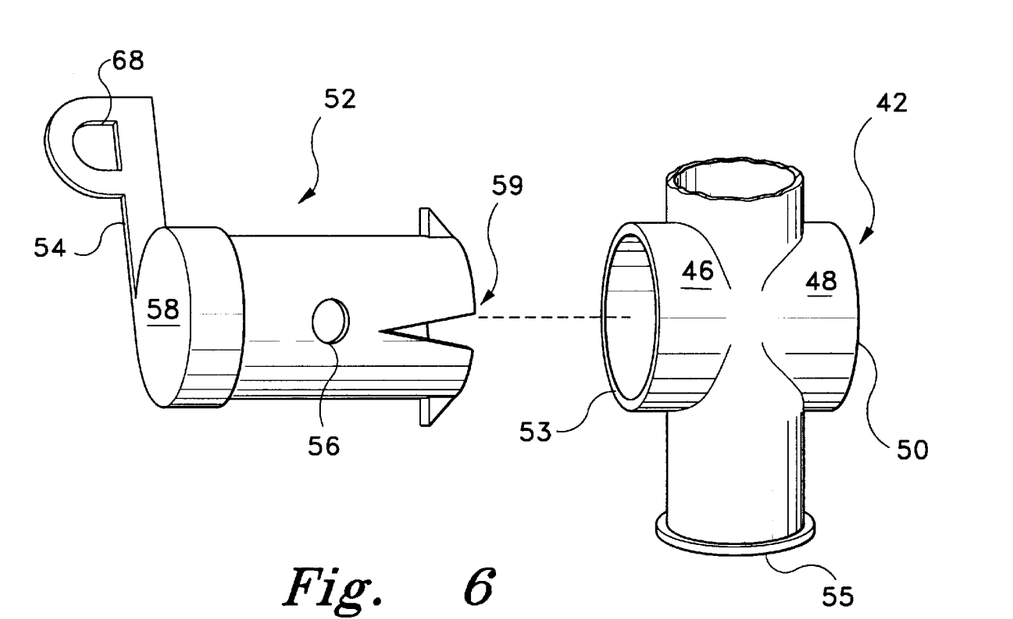
FIG. 6 is an exploded view of the flush valve of the access sheath.
Figure 7:
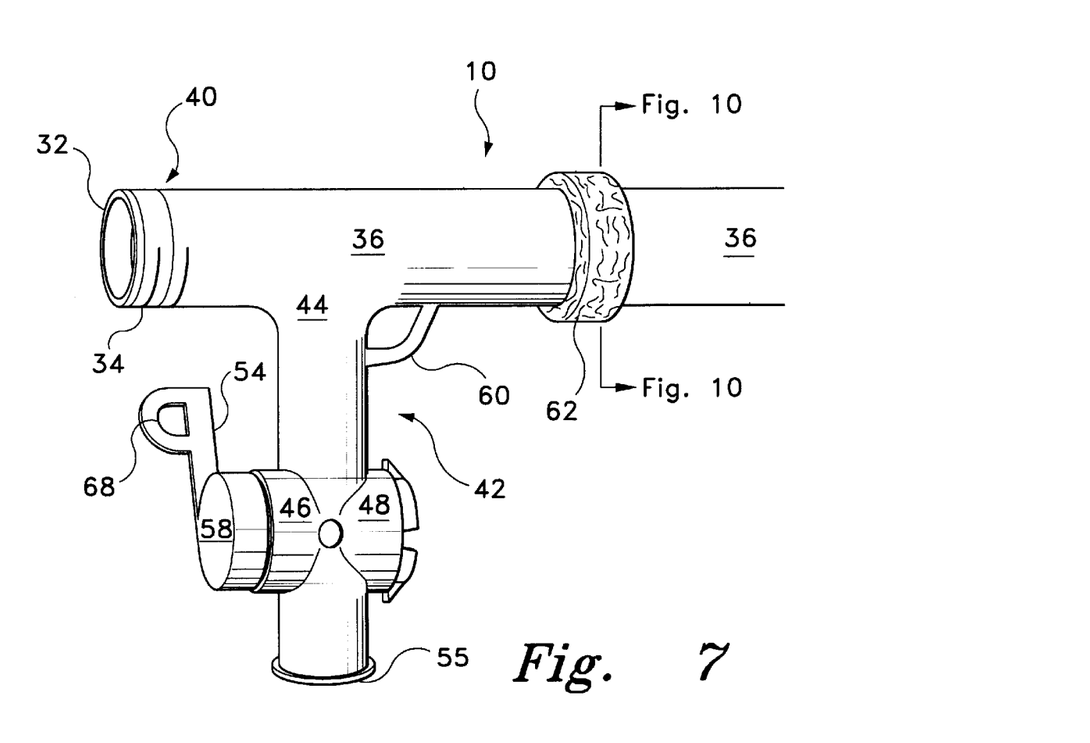
FIG. 7 is a partial perspective view of the access sheath of the present invention.
Figure 8:
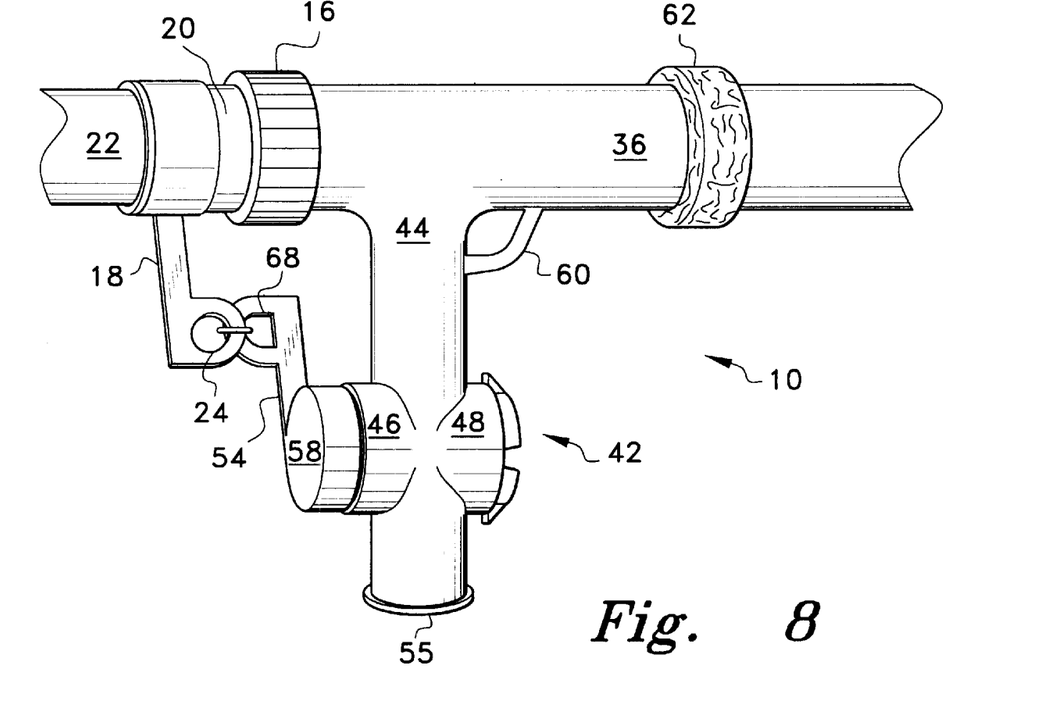
FIG. 8 is a partial perspective view of the hemodialysis access sheath and catheter engaged and locked into place.

The access sheath 10 has a T-shaped side tube 42 having a base 44, a first side arm 46 with a first side orifice 53, a second side arm 48 with a second side orifice 50 opposite the first side orifice 52, and an access orifice 55 opposite the base 44 as shown in FIGS. 6, 7 and 8. The base 44 is disposed at an angle to the elongated tube 36 and adjoining the proximal end 40 thereof.

The side tube 42 has the arms 46 and 48 aligned with and in the same plane as the elongated tube 36. The side tube 42 has a flush valve 52 rotatably inserted into the first side orifice 53 extending therethrough the first and second arms 46 and 48 to the second side orifice 50. The flush valve 52 has a flush lever 54 and a syringe orifice 56. The flush valve 52 being of a cylindrical shape having two sides 58 and 59, as shown in FIG. 6, with the syringe orifice 56 being an opening extending perpendicular through the cylindrical shape such that when the syringe orifice 56 is exposed at the access orifice 55 there is an opening into the T-shaped side tube 42 through to the elongated tube 36 and when the syringe orifice 56 is not exposed at the access orifice 55 the T-shaped side tube 42 is closed and sealed.

The flush lever 54 is disposed on and attached to the side 58 of the cylindrical shape of the flush valve 52 towards the proximal end 40 of the elongated tube 36 in order to facilitate the opening and closing of the t-shaped side tube 42 with the closed position having the flush lever 54 laying alongside the t-shaped side tube 42 thus approaching the elongated tube 36 and the open position having the flush lever 42 perpendicular to the t-shaped side tube 42. Ideally, the flush lever 54 of the flush valve 52 has a second interlocking tab 68.

In order to avoid having the flush valve 52 open accidently, a means for attaching and interconnecting the second interlocking tab 68 with the first interlocking tab 24 is essential, as shown in FIG. 8. The two tabs 24 and 68 can be attached by stitches, wire ties, plastic ties, staples, or other means.

A stitch loop 60 interconnects towards the distal side 38 of the elongated tube 36 and the base 44 of the side tube 42 for receiving means to surgically secure the access sheath 10 to the patient. The stitch loop 60 may be secured by stitches, staples or other surgical means and is designed to hold the access sheath 10 in place until the patients body can heal around the access sheath 10 and enclose it. A Dacron™ polyester fiber cuff 62 circumnavigating the elongated tube 36 distal to the stitch loop 60 is provided for the patients body to attach to and heal around thus securing the access sheath 10 in the patients body. The Dacron™ polyester fiber cuff 62 is clearly shown in FIGS. 10 and 11.

The access sheath 10 comes in a variety of lengths for optimization of placement. After venipuncture, a 0.035 wire is placed. The tract is dilated. An inner introducer with the dilator-access sheath combined is advanced into a central vein. The introducer is then removed. A stitch is placed in the stitch loop 60 and secures the sheath until ingrowth into the Dacron™ polyester fiber cuff 62 is established. The hemodialysis catheter 12 is placed through the access sheath 10 with the hub being rotated onto the threaded lip of the sheath orifice. The flush valve is closed and secured into place by the interlocking tabs to prevent accidental removal of the hemodialysis catheter 12 and inadvertent opening of the flush valve. To replace a malfunctioning hemodialysis catheter 12, a physician removes the stitch or cable tie securing the flange and valve lever, twists the hub and removes the catheter 12. The sheath is flushed out and a new catheter is inserted and secured in place as before.

What is claimed is:

1. A hemodialysis access sheath comprising:
   a sheath having an elongated tube;
      the elongated tube having a distal end and a proximal end;
      the distal end having a tapered opening;
   a sheath orifice disposed on the proximal end of the elongated tube;
      the sheath orifice having a threaded lip and a thin slit membrane disposed inside the sheath orifice;
   a side t-shaped tube having a base, a first side arm with a first side orifice, a second side arm with a second side orifice opposite the fist side orifice, and an access orifice opposite the base;
      the base disposed at an angle to the elongated tube adjoining the proximal end thereof;
      the side tube having the arms of the t-shape aligned with the elongated tube;
      the side tube having a flush valve rotatably inserted into the first side orifice extending therethrough to the second side orifice;
      the flush valve having a flush lever and a syringe orifice, said flush valve being convertible between an open and a closed position, wherein the open position allows the passage of liquids through said t-shaped tube and the closed position prevents the passage of liquids through said t-shaped tube;
      the flush valve being of a cylindrical shape having two sides with the syringe orifice being an opening extending perpendicular through the cylindrical shape such that when the syringe orifice is exposed at the access orifice there is an opening into the t-shaped side tube through to the elongated tube and when the syringe orifice is not exposed at the access orifice the t-shaped side tube is closed and sealed;
      the flush lever is disposed on one said side of the cylindrical shape towards the proximal end of the elongated tube in order to facilitate opening and closing of the t-shaped side tube with the closed position having the flush lever laying alongside the t-shaped tube thus approaching the elongated tube and the open position having the flush lever perpendicular to the t-shaped tube;
   a stitch loop interconnecting the distal side of the elongated tube and the base of the side tube for receiving means to surgically secure the access sheath to the patient; and
   a polyester fiber cuff circumnavigating the elongated tube distal to the stitch loop.

2. The access sheath according to claim 1, further comprising:
   a hemodialysis catheter and an adapter;
      the adapter having a hub, a flange, a first restriction band, and a second restriction band;
   the hemodialysis catheter having a catheter tube, a distal end, and a proximal end;
      the hub rotatably circumnavigates the tube of the catheter and having the threaded receptor opened towards the distal end for receiving the threaded lip of the sheath orifice;
      the flange rotatably circumnavigates the catheter tube proximal the hub; and
      the flange is flanked by the first and second restriction bands thus preventing lateral movement of the flange along the catheter tube.

3. The access sheath according to claim 2, further comprising:
   the flush lever of the flush valve having a second interlocking tab; and
   the flange having a first interlocking tab for receiving attachment means to interconnect the second interlocking tab with the first interlocking tab.

4. A hemodialysis access sheath and an adapter for a hemodialysis catheter comprising:
   a sheath having an elongated tube;
      the elongated tube having a distal end and a proximal end;
      the distal end having a tapered opening;
   a sheath orifice disposed on the proximal end of the elongated tube;
      the sheath orifice having a threaded lip and a thin slit membrane disposed inside the sheath orifice;
   a side t-shaped tube having a base, a first side arm with a first side orifice, a second side arm with a second side orifice opposite the fist side orifice, and an access orifice opposite the base;
      the base disposed at an angle to the elongated tube adjoining the proximal end thereof;
      the side tube having the arms of the t-shape aligned with the elongated tube;
      the side tube having a flush valve rotatably inserted into the first side orifice extending therethrough to the second side orifice;
      the flush valve having a flush lever and a syringe orifice, said flush valve being convertible between an open and a closed position, wherein the open position allows the passage of liquids through said t-shaped tube and the closed position prevents the passage of liquids through said t-shaped tube;
         the flush valve being of a cylindrical shape having two sides with the syringe orifice being an opening extending perpendicular through the cylindrical shape such that when the syringe orifice is exposed at the access orifice there is an opening into the t-shaped side tube through to the elongated tube and when the syringe orifice is not exposed at the access orifice the t-shaped side tube is closed and sealed;
         the flush lever is disposed on one said side of the cylindrical shape towards the proximal end of the elongated tube in order to facilitate opening and closing of the t-shaped side tube with the closed position having the flush lever laying alongside the t-shaped tube thus approaching the elongated tube and the open position having the flush lever perpendicular to the t-shaped tube;
   a stitch loop interconnecting the distal side of the elongated tube and the base of the side tube for receiving means to surgically secure the access sheath to the patient; and
   a polyester fiber cuff circumnavigating the elongated tube distal to the stitch loop.
   a hemodialysis catheter and an adapter;
      the adapter having a hub, a flange, a first restriction band, and a second restriction band;
   the hemodialysis catheter having a catheter tube, a distal end, and a proximal end;
      the hub rotatably circumnavigates the tube of the catheter and having the threaded receptor opened towards the distal end for receiving the threaded lip of the sheath orifice;

the flange rotatably circumnavigates the catheter tube proximal the hub; and the flange is flanked by the first and second restriction bands thus preventing lateral movement of the flange along the catheter tube;

the flush lever of the flush valve having a second interlocking tab; and the flange having a first interlocking tab for receiving attachment means to interconnect the second interlocking tab with the first interlocking tab.

5. A hemodialysis access sheath comprising, in combination with a hemodialysis catheter:

a sheath having an elongated tube;

the elongated tube having a distal end and a proximal end;

the distal end having a tapered opening;

a sheath orifice disposed on the proximal end of the elongated tube;

the sheath orifice having a threaded lip and a thin slit membrane disposed inside the sheath orifice;

a side t-shaped tube having a base, a first side arm with a first side orifice, a second side arm with a second side orifice opposite the fist side orifice, and an access orifice opposite the base;

the base disposed at an angle to the elongated tube adjoining the proximal end thereof;

the side tube having the arms of the t-shape aligned with the elongated tube;

the side tube having a flush valve rotatably inserted into the first side orifice extending therethrough to the second side orifice;

the flush valve having a flush lever and a syringe orifice, said flush valve being moveable between an open and a closed position; wherein the open position allows the passage of liquids through said t-shaped tube and the closed position prevents the passage of liquids through said t-shaped tube;

the flush valve being of a cylindrical shape having two sides with the syringe orifice being an opening extending perpendicular through the cylindrical shape such that when the syringe orifice is exposed at the access orifice there is an opening into the t-shaped side tube through to the elongated tube and when the syringe orifice is not exposed at the access orifice the t-shaped side tube is closed and sealed;

the flush lever is disposed on one said side of the cylindrical shape towards the proximal end of the elongated tube in order to facilitate opening and closing of the t-shaped side tube with the closed position having the flush lever laying alongside the t-shaped tube thus approaching the elongated tube and the open position having the flush lever perpendicular to the t-shaped tube;

a stitch loop interconnecting the distal side of the elongated tube and the base of the side tube for receiving means to surgically secure the access sheath to the patient; and a polyester fiber cuff circumnavigating the elongated tube distal to the stitch loop.

6. The access sheath according to claim 5, further comprising, wherein the catheter includes:

an adapter; the adapter having a hub, a flange, a first restriction band, and a second restriction band;

the hemodialysis catheter having a catheter tube, a distal end, and a proximal end;

the hub rotatably circumnavigates the tube of the catheter and having the threaded receptor opened towards the distal end for receiving the threaded lip of the sheath orifice;

the flange rotatably circumnavigates the catheter tube proximal the hub; and the flange is flanked by the first and second restriction bands thus preventing lateral movement of the flange along the catheter tube.

7. The access sheath according to claim 6, further comprising:

the flush lever of the flush valve having a second interlocking tab; and the flange having a first interlocking tab for receiving attachment means to interconnect the second interlocking tab with the first interlocking tab.

* * * * *